United States Patent [19]

Umemura et al.

[11] 4,421,925
[45] Dec. 20, 1983

[54] 4-ALKOXY-1,3-DIOXANE-5-CARBONITRILES AND PROCESS FOR PREPARING THE SAME

[75] Inventors: Sumio Umemura; Kozo Fujii; Keigo Nishihira; Hiroyuki Sawada; Shuji Tanaka; Mamoru Nakai; Hiroshi Yoshida; Yoshiaki Kuroki, all of Ube, Japan

[73] Assignee: Ube Industries, Ltd., Ube, Japan

[21] Appl. No.: 375,203

[22] Filed: May 5, 1982

[30] Foreign Application Priority Data

May 19, 1981 [JP] Japan .................................. 56-74194
Sep. 30, 1981 [JP] Japan ................................. 56-153814
Oct. 12, 1981 [JP] Japan ................................. 56-160986

[51] Int. Cl.³ ........................................... C07D 319/06
[52] U.S. Cl. ................................................... 549/372
[58] Field of Search ......................................... 549/372

[56] References Cited

U.S. PATENT DOCUMENTS 2,628,257  2/1953  Hoaglin et al. ..................... 549/372
4,320,024  3/1982  Reierson et al. .................... 549/372

OTHER PUBLICATIONS

Abraham et al., Journ. Amer. Chem. Soc. 94, pp. 1913–1918.

Primary Examiner—Ethel G. Love
Attorney, Agent, or Firm—Frishauf, Holtz, Goodman & Woodward

[57] ABSTRACT

There are disclosed a 4-alkoxy-1,3-dioxane-5-carbonitrile which is a novel compound represented by the formula

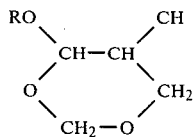

wherein R represents a lower-alkyl group, and which is useful as an intermediate for the synthesis of Vitamin $B_1$, and a process for preparing the novel compound by subjecting a 3-alkoxy-2-propenenitrile to reaction with a formaldehyde in the presence of an acid catalyst.

11 Claims, No Drawings

4-ALKOXY-1,3-DIOXANE-5-CARBONITRILES AND PROCESS FOR PREPARING THE SAME

This invention relates to a 4-alkoxy-1,3-dioxane-5-carbonitrile and a process for preparing the same.

The 4-alkoxy-1,3-dioxane-5-carbonitrile according to the present invention is a novel compound represented by the general formula [I]:

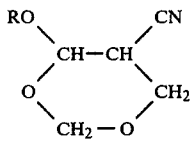 [I]

wherein R represents a lower-alky group.

This compound may easily be converted into a starting material for the synthesis of Vitamin $B_1$ by a conventional method such as hydrolysis, etherification, alcoholysis and so on.

For example, propanenitriles such as a 2-dialkoxymethyl-3-alkoxypropanenitrile, a 2-alkoxymethylene-3-alkoxypropanenitrile and a 2-methylene-3,3-dialkoxy-propanenitrile which have been known as starting materials for the synthesis of Vitamin $B_1$ may be prepared by subjecting a 4-alkoxy-1,3-dioxane-5-carbonitrile to reaction with an alcohol at a temperature of 40° to 150° C. in the presence of an acid catalyst such as concentrated sulfuric acid, concentrated hydrochloric acid, hydrogen chloride, p-toluenesulfonic acid and a solid acid.

The 4-alkoxy-1,3-dioxane-5-carbonitrile of the formula [I] can be prepared by subjecting a 3-alkoxy-2-propenenitrile to reaction with formaldehyde in the presence of an acid catalyst.

Conventionally, the process for the preparation of a 1,3-dioxane by subjecting an olefin substituted by an alkyl group, an aryl group, a halogen atom or the like to reaction with an aldehyde in the presence of an acid catalyst has been known as the Prince reaction.

However, a Prince reaction of an nitrile-group-substituted olefin has never been known, nor is there any literature which has suggested that a 4-alkoxy-1,3-dioxane-5-carbonitrile could be obtained if such a specific olefin be subjected to the Prince reaction.

The process for the preparation of the compound having the formula [I] will be described in detail below.

The 3-alkoxy-2-propenenitrile to be used is represented by the general formula

RO—CH=CH—CN (wherein R represents a lower-alkyl group such as methyl, ethyl, propyl, butyl, etc.).

As specific examples, there may be mentioned 3-methoxy-2-propenenitrile, 3-ethoxy-2-propenenitrile, 3-n(or i)-propoxy-2-propenenitrile, 3-n(i, sec or tert)-butoxy-2-propenenitrile and the like.

As the formaldehyde, there may be used any compound which forms formaldehyde in the reaction system, such as paraformaldehyde, trioxane, tetraoxane, polyoxymethylene, methylal, methylene diacetate and the like.

The formaldehyde may be employed in an amount (calculated in terms of the aldehyde) of 1 to 20 moles, preferably 2 to 10 moles based on one mole of the 3-alkoxy-2-propenenitrile.

The catalyst is not specifically limited as long as it is a general acid catalyst.

As the specific examples of the acid catalysts, there may be mentioned a Lewis acid catalyst such as $AlCl_3$, $BF_3$, $BF_3 \cdot (C_2H_5)_2O$, $BF_3 \cdot (CH_3COOH)_2$, $BF_3 \cdot (CH_3OH)_2$,

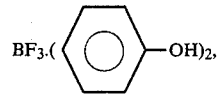

$BF_3 \cdot C_2H_5NH_2$, $FeCl_3$, $FeCl_2$, $ZnCl_2$, $SnCl_2$, $CuCl_2$, $CuCl$, $TiCl_4$, and $TiCl_3$; a mineral acid catalyst such as $H_2SO_4$, $HCl$ and $H_3PO_4$; a solid acid catalyst such as clayish mineral, silica-alumina, silica-boria, silica-magnesia, solidified acid, cation-exchange resin, sulfate, phosphate and heteropoly-acid; and so on.

Among these catalysts, boron trifluoride and its complex salts are particularly preferred since they can give the desired product according to this invention in high yield and selectivity. In particular, much higher yield and selectivity can be attained when the reaction is carried out in an aprotic solvent. The reaction is preferably carried out in the presence of boron trifluoride or its complex salt as the catalyst by using the formaldehyde in a gaseous state.

In cases where the acid catalyst is composed of a Lewis acid or a mineral acid, it may be used in an amount of 0.001 to 10 moles, preferably 0.01 to 5 moles based on one mole of the 3-alkoxy-2-propenenitrile. In cases where the acid catalyst is composed of a solid acid, it may be used in an amount of 0.01 to 10 parts by weight, preferably 0.05 to 5 parts by weight, based on one part by weight of the 3-alkoxy-2-propenenitrile. When the amount of the acid catalyst to be used is less than the above-mentioned lower limit, the reaction proceeds too slowly, and when it is more than the above-mentioned upper limit, amounts of by-products increase.

The reaction according to the present invention may be carried out either in a gaseous phase or in a liquid phase, and may be practiced either by a batch system or by a continuous (flow) system.

In cases where the reaction is carried out in a liquid phase, it may be carried out without any solvent. However, in order to make the reaction proceed smoothly, it may preferably be carried out in a solvent. As the solvent to be used, there may be mentioned an ether group solvent such as dioxane, tetrahydrofuran, dimethoxyethane, diethyl ether, diisopropyl ether and dibutyl ether; a hydrocarbon group solvent such as benzene, toluene, xylene, hexane, heptane, cyclohexane, cycloheptane, tetralin, decalin and nitrobenzene; a halogenated hydrocarbon group solvent such as methylene chloride, chloroform, carbon tetrachloride and 1,2-dichloroethane; a nitrile group solvent such as acetonitrile, propionitrile and benzonitrile; an organic acid group solvent and its ester such as acetic acid, propionic acid, methyl acetate, ethyl acetate and butyl acetate; an alcohol group solvent such as methanol, ethanol, propanol and butanol; water; and so on.

As the aprotic solvent which is particularly preferred if it is used in combination with boron trifluoride or its complex salt as the catalyst, there may be mentioned, for example, an ether group solvent, a hydrocarbon group solvent, a halogenated hydrocarbon group solvent, a nitrile group solvent, an ester group solvent as enumerated above.

The solvent may preferably be employed in an amount of 5 to 100 parts by weight based on one part by weight of the 3-alkoxy-2-propenenitrile. When the amount of the solvent to be used is less than the above-mentioned lower limit, the yield of the desired product decreases. When it is more than the above-mentioned upper limit, the amount of the solvent to be recovered is increased so that the recovery thereof would be uneconomical industrially, while the yield of the desired product is not badly affected.

When a formaldehyde gas is used as the starting material, the reaction may be carried out by, for instance, one of the following procedures.

Namely, after blowing a formaldehyde gas into a solvent to make it absorb the gas, the catalyst and the 3-alkoxy-2-propenenitrile are added thereto. Alternatively, after the catalyst is made to exist in the solvent and then the formaldehyde gas is blown thereinto, the 3-alkoxy-2-propenenitrile is added thereto. As a further alternative procedure, after the 3-alkoxy-2-propenenitrile is dissolved in the solvent and the catalyst is added thereto, the formaldehyde gas is blown thereinto.

The reaction may be carried out at a temperature of $-20°$ to $300°$ C., preferably $0°$ to $250°$ C., under ordinary pressure or under positive pressure for 1 to 24 hours. The isolation and purification of the desired reaction product may be carried out by optionally adopting such procedure as filtration, extraction and distillation.

The present invention will be explained in more detail by way of the following Examples and Referential Example.

EXAMPLE 1

In a 500 ml flask equipped with a thermometer and a calcium chloride tube, there were placed 8.31 g (100 mmoles) of 3-methoxy-2-propenenitrile and 300 g of dioxane (solvent), and 13.3 g (100 mmoles) of $AlCl_3$ was added to the mixture with stirring the mixture at a temperature of $15°$ C. After 7.51 g (250 mmoles) of paraformaldehyde was added thereto at the same temperature, the reaction was carried out at a temperature of $25°$ C. for 18 hours. After the resulting reaction mixture was poured into 300 ml of an ice-water, the mixture was extracted three times with 200 ml of ethyl ether. The resulting extract was washed with a saturated saline solution and then dried over sodium sulfate. After the sodium sulfate was removed by filtration, the filtrate was distilled under reduced pressure to give 6.58 g of a colorless liquid having a boiling point of $85°$ to $87°$ C. (at 5 mmHg).

From the data of its NMR, IR, MS and elementary analysis, it was identified as 4-methoxy-1,3-dioxane-5-carbonitrile.

EXAMPLES 2 TO 23

In a 50 ml flask equipped with a thermometer and a calcium chloride tube, there were placed 0.831 g (10 mmoles) of 3-methoxy-2-propenenitrile and a predetermined amount of each solvent, and each catalyst was added to the mixture with stirring it at a temperature of $15°$ C.

Subsequently, after addition of a predetermined amount of each aldehyde thereto at the same temperature, the reaction was carried out at a predetermined temperature for a predetermined hour. The thus obtained reaction mixture was analyzed by gas-chromatography to observe the conversion of the starting 3-methoxy-2-propenenitrile and the selectivity to the produced 4-methoxy-1,3-dioxane-5-carbonitrile.

The reaction conditions and the results are shown in Table 1.

TABLE 1

| | Catalyst | | Solvent | | Aldehyde | | Reaction | | Conversion of starting 3-methoxy-2-propenenitrile (%) | Selectivity to produced 4-methoxy-1,3-dioxane-5-carbonitrile (%) |
|---|---|---|---|---|---|---|---|---|---|---|
| Example | Kind | Amount (mmole) | Kind | Amount (g) | Kind | Amount (mmole) | Temp. (°C.) | Time (hr) | | |
| 2 | $BF_3 \cdot (C_2H_5)_2O$ | 3 | dioxane | 15 | paraformaldehyde | 25 | 60 | 5 | 100 | 65 |
| 3 | $AlCl_3$ | 10 | acetonitrile | 10 | paraformaldehyde | " | 25 | 18 | " | 40 |
| 4 | " | " | methylene chloride | 20 | paraformaldehyde | 30 | " | 12 | 95 | 30 |
| 5 | " | " | dioxane | 30 | tetraoxane | 25 | " | 18 | 95 | 55 |
| 6 | " | " | " | 5 | polyoxymethylene | " | " | 6 | 97 | 33 |
| 7 | " | " | " | 30 | formaldehyde | 33 | " | 4 | 96 | 40 |
| 8 | $BF_3 \cdot (C_2H_5)_2O$ | 3 | " | 15 | paraformaldehyde | 25 | 80 | 6 | 100 | 49 |
| 9 | " | " | " | 30 | paraformaldehyde | " | 60 | 3 | 98 | 74 |
| 10 | " | 3 | dioxane | 50 | paraformaldehyde | 25 | 60 | 9 | 94 | 82 |
| 11 | " | " | " | 15 | paraformaldehyde | 15 | " | 6 | 86 | 52 |
| 12 | " | " | " | " | paraformaldehyde | 50 | " | 3 | 96 | 57 |
| 13 | " | 1 | " | " | paraformaldehyde | 25 | " | 2.5 | 85 | 54 |
| 14 | " | " | " | 30 | paraformaldehyde | " | " | 10 | 84 | 61 |
| 15 | " | " | " | 50 | paraformaldehyde | " | " | 6 | 89 | 76 |

TABLE 1-continued

| Example | Catalyst Kind | Catalyst Amount (mmole) | Solvent Kind | Solvent Amount (g) | Aldehyde Kind | Aldehyde Amount (mmole) | Reaction Temp. (°C.) | Reaction Time (hr) | Conversion of starting 3-methoxy-2-propene-nitrile (%) | Selectivity to produced 4-methoxy-1,3-dioxane-5-carbo-nitrile (%) |
|---|---|---|---|---|---|---|---|---|---|---|
| 16 | " | 0.5 | " | 30 | paraform-aldehyde | " | " | 20 | 87 | 63 |
| 17 | " | 1 | xylene | " | paraform-aldehyde | " | 80 | 2 | 85 | 45 |
| 18 | " | " | dimethoxy-ethane | " | paraform-aldehyde | " | 60 | 4 | 43 | 48 |
| 19 | " | 1.5 | ethyl acetate | " | paraform-aldehyde | 20 | 65 | " | 99 | 76 |
| 20 | BF$_3$.(CH$_3$COOH)$_2$ | 3.0 | dioxane | " | paraform-aldehyde | 25 | 60 | 3 | 97 | 77 |
| 21 | " | 1.0 | acetic acid | 30 | paraform-aldehyde | 25 | 60 | 9 | 91 | 48 |
| 22 | SnCl$_4$ | 5 | aceto-nitrile | 10 | paraform-aldehyde | " | 25 | 10 | 90 | 30 |
| 23 | SnCl$_2$ | " | acetic acid | 15 | paraform-aldehyde | " | 70 | 4.5 | 85 | 32 |

EXAMPLE 24

In the same reaction apparatus as in Example 1, there were charged 12.5 g (100 mmoles) of 3-n-butoxy-2-propenenitrile and 300 g of dioxane (solvent), and, with stirring the resulting mixture at a temperature of 15° C., 2.13 g (15 mmoles) of BF$_3$.(C$_2$H$_5$)$_2$O was added thereto. Subsequently, after 7.51 g (250 mmoles) of paraformaldehyde was added thereto at the same temperature, the reaction was carried out at a temperature of 60° C. for 6 hours. The resulting reaction mixture was cooled to room temperature, and then 10.6 g (100 mmoles) dried sodium carbonate was added thereto. After the mixture was stirred at room temperature for 3 hours, it was filtered, followed by distillation of the filtrate under reduced pressure to obtain 11.0 g of a colorless liquid having a boiling point of 108° to 110° C. (at 5 mmHg). The thus obtained compound was identified as 4-n-butoxy-1,3-dioxane-5-carbonitrile from the data of its NMR, IR and MS and from the result of its elementary analysis.

Specific examples of the novel 4-alkoxy-1,3-dioxane-5-carbonitrile of the present invention, which have been prepared according to the above-mentioned Examples, will be shown in the following Table 2.

TABLE 2

| Compound No. | Chemical name | Structural formula | Boiling point |
|---|---|---|---|
| 1 | 4-methoxy-1,3-dioxane-5-carbonitrile | CH$_3$O–CH–CH(CN)–CH$_2$–O–CH$_2$–O (ring) | 85–87° C./5mmHg |
| 2 | 4-ethoxy-1,3-dioxane-5-carbonitrile | C$_2$H$_5$O–CH–CH(CN)–CH$_2$–O–CH$_2$–O (ring) | 77–79° C./1.2mmHg |
| 3 | 4-n-propoxy-1,3-dioxane-5-carbonitrile | n-C$_3$H$_7$O–CH–CH(CN)–CH$_2$–O–CH$_2$–O (ring) | 98–100° C./3mmHg |
| 4 | 4-n-butoxy-1,3-dioxane-5-carbonitrile | n-C$_4$H$_9$O–CH–CH(CN)–CH$_2$–O–CH$_2$–O (ring) | 108–110° C./5mmHg |

EXAMPLE 25

In a 300 ml flask equipped with a thermometer, a calcium chloride tube, a gas inlet tube and a dropping funnel, there was charged 200 g of ethyl acetate, and 4.50 g (150 mmoles) of formaldehyde gas was blown thereinto to make it to be absorbed in the solvent, followed by the addition of 0.85 g (6 mmoles) of BF$_3$.(C$_2$H$_5$)$_2$O. After heating the resulting mixture up to 60° C., a solution which had been prepared by dissolving 5.00 g (60 mmoles) of 3-methoxy-2-propenenitrile in 20 g of ethyl acetate was added dropwise thereto at a temperature of 60° C. over 2 hours.

After stirring for further 2 hours at a temperature of 60° C., the resulting reaction mixture was subjected to quantitative analysis by gas chromatography.

EXAMPLE 26

An experiment was run in the same manner as in Example 25 except that the amounts of ethyl acetate and $BF_3.(C_2H_5)_2O$ to be charged were changed to be 130 g and 0.43 g (3 mmoles), respectively.

EXAMPLE 27

An experiment was run in the same manner as in Example 26 except that the amount of ethyl acetate to be charged was changed to be 80 g.

EXAMPLE 28

An experiment was run in the same manner as in Example 26 except that $BF_3.(CH_3COOH)_2$ was used as the catalyst in an amount of 0.56 g (3 mmoles).

EXAMPLE 29

An experiment was run in the same manner as in Example 26 except that $BF_3.(CH_3OH)_2$ was used as the catalyst in an amount of 0.40 g (3 mmoles).

The results of Examples 25 to 29 are shown in the following Table 3.

EXAMPLE 31

An experiment was run in the same manner as in Example 30 except that acetonitrile was used in place of dioxane and that 7.50 g (60 mmoles) of 3-n-butoxy-2-propenenitrile was used in place of 3-ethoxy-2-propenenitrile.

As the result, it was found that the conversion of the 3-n-butoxy-2-propenenitrile was 90.2% and that the 4-n-butoxy-1,3-dioxane-5-carbonitrile was produced in a selectivity of 91.8%.

EXAMPLE 32

An experiment was run in the same manner as in Example 25 except that methylene chloride was used in place of ethyl acetate; the reaction temperature was maintained at 40° C.; a solution of 3-methoxy-2-propenenitrile in methylene chloride was added over 4 hours; and the mixture was stirred for 8 hours.

As the result, it was found that the conversion of the 3-methoxy-2-propenenitrile was 84.9% and that the 4-methoxy-1,3-dioxane-5-carbonitrile was produced in a selectivity of 95.7%.

EXAMPLE 33

In the same apparatus as in Example 25, there was charged a solution which had been prepared by dissolving 0.20 g (3 mmoles) of $BF_3$ in 200 g of ethyl acetate, and then 4.50 g (150 mmoles) of a formaldehyde gas was blown thereinto at room temperature.

TABLE 3

| Example | Total amount of solvent (ethyl acetate) (g) | Kind of catalyst and its charged amount (g) | Aldehyde as starting material | Conversion of used 3-methoxy-2-propenenitrile (%) | Selectivity to produced 4-methoxy-1,3-dioxane-5-carbonitrile (%) |
|---|---|---|---|---|---|
| 25 | 220 | $BF_3.(C_2H_5)_2O$ 0.85 | Formaldehyde gas | 100 | 91.5 |
| 26 | 150 | $BF_3.(C_2H_5)_2O$ 0.43 | " | 98.5 | 95.3 |
| 27 | 100 | $BF_3.(C_2H_5)_2O$ 0.43 | " | 94.5 | 90.3 |
| 28 | 150 | $BF_3.(CH_3COOH)_2$ 0.56 | " | 97.1 | 93.6 |
| 29 | " | $BF_3.(CH_3OH)_2$ 0.40 | " | 99.0 | 91.7 |

EXAMPLE 30

In a 300 ml flask equipped with a thermometer, a reflux condenser equipped with a calcium chloride tube, a gas-inlet tube and a dropping funnel, there was charged 130 g of dioxane. Then, 4.50 g (150 mmoles) of a formaldehyde gas was blown thereinto at room temperature to make it to be absorbed, followed by the addition of 0.43 g (3 mmoles) of $BF_3.(C_2H_5)_2O$. After heating the resulting mixture up to 60° C., a solution which had been prepared by dissolving 5.83 g (60 mmoles) of 3-ethoxy-2-propenenitrile in 20 g of dioxane was added dropwise thereto at 60° C. over 2 hours.

After stirring for further 2 hours at 60° C., the resulting reaction mixture was subjected to quantitative analysis by gas chromatography.

As the result, it was found that the conversion of the 3-ethoxy-2-propenenitrile was 93.3% and that the 4-ethoxy-1,3-dioxane-5-carbonitrile was produced in a selectivity of 91.0%.

After the mixture was heated up to 60° C., a solution which had been prepared by dissolving 5.00 g (60 mmoles) of 3-methoxy-2-propenenitrile in 20 g of ethyl acetate was added dropwise thereto at 60° C. over 2 hours. After stirring for further 2 hours at 60° C., the resulting reaction mixture was subjected to quantitative analysis by gas chromatography.

As the result, it was found that the conversion of the 3-methoxy-2-propenenitrile was 96.3% and that the 4-methoxy-1,3-dioxane-5-carbonitrile was produced in a selectivity of 93.1%.

Next, there will be shown as a Referential Example an example of preparation of a propanenitrile which has been known as a starting material for the snythesis of Vitamine $B_1$ from the 4-alkoxy-1,3-dioxane-5-carbonitrile of the present invention.

Referential Example

In a 50 ml flask equipped with a reflux condenser, there were charged a solution of 2.58 g (25 mmoles) of conc. sulfuric acid in 8.0 g (250 mmoles) of methanol, 1.43 g (10 mmoles) of 4-methoxy-1,3-dioxane-5-carbonitrile and 16 g of dioxane (solvent), and the reaction was carried out under reflux for 6 hours with stirring of the mixture.

As the result, the conversion of 4-methoxy-1,3-dioxane-5-carbonitrile was 100%; and 2-dimethoxymethyl-3-methoxypropanenitrile, 2-methoxymethylene-3-methoxypropanenitrile and 2-methylene-3,3-dimethoxy-propanenitrile were obtained in selectivities of 64.1%, 14.9% and 12.3%, respectively.

We claim:

1. A 4-alkoxy-1,3-dioxane-5-carbonitrile represented by the formula

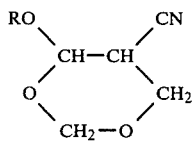

wherein R represents a lower-alkyl group.

2. A 4-alkoxy-1,3-dioxane-5-carbonitrile as claimed in claim 1 wherein R represents a methyl group, an ethyl group, an n-propyl group, an isopropyl group, an n-butyl group, an isobutyl group a sec-butyl group, or a tert-butyl group.

3. A process for preparing a 4-alkoxy-1,3-dioxane-5-carbonitrile of the formula

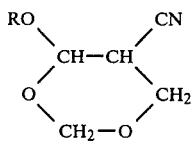

wherein R is a lower-alkyl group,
which comprises reacting at a temperature between −20° C. and 300° C. a 3-alkoxy-2-propenenitrile of the formula RO—CH═CH—CN with formaldehyde in the presence of an acid catalyst, said formaldehyde being in an amount of 1 to 20 moles in terms of the aldehyde based on one mole of the 3-alkoxy-2-propenenitrile.

4. A process for preparing a 4-alkoxy-1,3-dioxane-5-carbonitrile of the formula

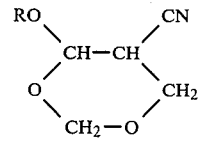

wherein R is a lower-alkyl group,
which comprises reacting at a temperature between −20° C. and 300° C. a 3-alkoxy-2-propenenitrile of the formula RO—CH═CH—CN with gaseous formaldehyde in an aprotic solvent in the presence of boron trifluoride or its complex salt as a catalyst, said formaldehyde being in an amount of 1 to 20 moles in terms of the aldehyde based on one mole of the 3-alkoxy-2-propenenitrile.

5. The process as claimed in claim 3 or 4 wherein said formaldehyde is formed from a compound selected from the group consisting of paraformaldehyde, trioxane, tetraoxane, polyoxymethylene, methylal, and methylene diacetate.

6. The process as claimed in claim 3 or 4 wherein formaldehyde is in an amount of 2 to 10 moles in terms of the aldehyde based on one mole of the 3-alkoxy-2-propenenitrile.

7. The process as claimed in claim 3 or 4 wherein the catalyst is in an amount of 0.001 to 10 moles based on one mole of the 3-alkoxy-2-propenenitrile when the catalyst is a Lewis acid or a mineral acid.

8. The process as claimed in claim 7 wherein the catalyst is in an amount of 0.01 to 5 moles based on one mole of the 3-alkoxy-2-propenenitrile.

9. The process as claimed in claim 3 or 4 wherein the catalyst is in an amount of 0.01 to 10 parts by weight based on one part by weight of the 3-alkoxy-1,3-propenenitrile when the catalyst is a solid acid.

10. The process as claimed in claim 9 wherein the catalyst is in an amount of 0.05 to 5 parts by weight based on one part by weight of the 3-alkoxy-2-propenenitrile.

11. The process as claimed in claim 6 wherein the reaction is carried out at a temperature of 0° to 250° C.

* * * * *